US008092830B2

(12) United States Patent
Yamamoto et al.

(10) Patent No.: US 8,092,830 B2
(45) Date of Patent: *Jan. 10, 2012

(54) LACTIC ACID POLYMER AND PROCESS FOR PRODUCING THE SAME

(75) Inventors: Kohei Yamamoto, Kawagoe (JP); Tsutomu Tani, Kawagoe (JP); Takashi Aoki, Kawagoe (JP); Yoshio Hata, Hokkaido (JP)

(73) Assignees: Wako Pure Chemical Industries, Ltd., Osaka (JP); Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/822,128

(22) Filed: Jul. 2, 2007

(65) Prior Publication Data

US 2007/0259036 A1 Nov. 8, 2007

Related U.S. Application Data

(60) Continuation of application No. 11/348,464, filed on Feb. 7, 2006, now abandoned, which is a division of application No. 10/344,131, filed as application No. PCT/JP01/06721 on Aug. 6, 2001, now Pat. No. 7,019,106.

(30) Foreign Application Priority Data

Aug. 7, 2000 (JP) ................................ 2000-238051

(51) Int. Cl.
 *A61K 9/50* (2006.01)
 *A61K 9/52* (2006.01)
 *C08G 63/44* (2006.01)
 *C08F 283/06* (2006.01)

(52) U.S. Cl. ........ 424/457; 424/423; 424/425; 424/451; 424/452; 424/486; 424/489; 514/963; 514/965; 525/410; 525/411; 525/413; 525/415; 528/354; 528/361; 528/480

(58) Field of Classification Search .................. 528/354, 528/361, 480; 525/410, 411, 413, 415; 424/423, 424/425, 451, 452, 457, 486, 489; 514/963, 514/965

See application file for complete search history.

(56) References Cited

U.S. PATENT DOCUMENTS

| | | | |
|---|---|---|---|
| 3,297,033 | A | 1/1967 | Schmitt et al. |
| 3,565,869 | A | 2/1971 | DeProspero et al. |
| 3,755,558 | A | 8/1973 | Scribner |
| 3,773,919 | A | 11/1973 | Boswell et al. |
| 3,839,297 | A | 10/1974 | Wasserman et al. |
| 3,890,283 | A | 6/1975 | Casey et al. |
| 3,912,692 | A | 10/1975 | Casey et al. |
| 4,249,531 | A | 2/1981 | Heller et al. |
| 4,273,920 | A | 6/1981 | Nevin |
| 4,479,911 | A | 10/1984 | Fong |
| 4,539,981 | A | 9/1985 | Tunc |
| 4,605,730 | A | 8/1986 | Shalaby et al. |
| 4,652,441 | A | 3/1987 | Okada et al. |
| 4,677,191 | A | 6/1987 | Tanaka et al. |
| 4,728,721 | A | 3/1988 | Yamamoto et al. |
| 4,767,628 | A | 8/1988 | Hutchinson |
| 4,789,726 | A | 12/1988 | Hutchinson |
| 4,801,739 | A | 1/1989 | Franz et al. |
| 4,849,228 | A | 7/1989 | Yamamoto et al. |
| 5,480,868 | A | 1/1996 | Kamei et al. |
| 5,585,460 | A | 12/1996 | Yamada et al. |
| 5,594,091 | A | 1/1997 | Igari et al. |
| 5,668,111 | A | 9/1997 | Kamei et al. |
| 5,763,513 | A | 6/1998 | Suzuki et al. |
| 5,922,682 | A | 7/1999 | Brich et al. |
| 6,113,943 | A | 9/2000 | Okada et al. |
| 6,353,086 | B1 | 3/2002 | Kolstad et al. |
| 6,362,308 | B1 | 3/2002 | Pham |
| 6,565,874 | B1 | 5/2003 | Dunn et al. |
| 6,703,477 | B2 | 3/2004 | Pham |
| 6,756,472 | B1 | 6/2004 | Hata et al. |
| 7,019,106 | B2 * | 3/2006 | Yamamoto et al. ........... 528/354 |
| 2003/0153724 | A1 | 8/2003 | Yamamoto et al. |

FOREIGN PATENT DOCUMENTS

DE 36 88 213 9/1993

(Continued)

OTHER PUBLICATIONS

Notice of Opposition to European Patent No. 1310517 dated Apr. 6, 2006 filed by Astellas Pharma Europe Ltd. and represented by Hoffmann-Elite of Munchen, Germany, including Facts and Evidence Supporting Opposition, pp. 1-24.

Letter of Hoffmann-Elite dated Jan. 2, 2007 representing Opponent Astellas Pharma, supplementing Notice of Opposition against European Patent No. 1310517, pp. 1-5.

Expert Opinion of Prof. Dr. Claus D. Eisenbach supporting Opponent Astellas Pharma in Opposition against European Patent No. 1310517, dated Apr. 6, 2006, labelled Exhibit 1, pp. 1-6, Tables 1-2, Figs. 1a-4 (Eisenbach I).

Curriculum Vitae of Prof. Dr. Claus D. Eisenbach supporting Opponent Astellas Pharma in Opposition against European Patent No. 1310517, dated Apr. 6, 2006, labelled Exhibit 2, pp. 1-29.

(Continued)

*Primary Examiner* — Ana Woodward
(74) *Attorney, Agent, or Firm* — Wenderoth Lind & Ponack, L.L.P.

(57) ABSTRACT

A process for producing a lactic acid polymer of 15,000 to 50,000 in weight-average molecular weight, the content of polymeric materials having not more than about 5,000 in weight-average molecular weight therein being not more than about 5% by weight, characterized by hydrolyzing a high molecular weight lactic acid polymer, placing the resultant solution comprising the hydrolyzed product under a condition capable of precipitating the objective lactic acid polymer, separating the precipitated lactic acid polymer and collecting them. The lactic acid polymer is useful as a matrix for sustained-release preparations. The sustained-release microcapsule preparation encapsulating a physiologically active substance can fully prevent the initial excessive release of the physiologically active substance from the microcapsules and keep a stable release rate over a long period of time.

12 Claims, No Drawings

FOREIGN PATENT DOCUMENTS

| | | |
|---|---|---|
| EP | 0 052 510 | 5/1982 |
| EP | 0 058 481 | 8/1982 |
| EP | 0 172 636 | 2/1986 |
| EP | 0 202 065 | 11/1986 |
| EP | 0 839 525 | 5/1988 |
| EP | 0 668 073 | 8/1995 |
| EP | 0 815 853 | 1/1998 |
| EP | 0 839 525 | 5/1998 |
| EP | 1 048 301 | 11/2000 |
| EP | 1 158 014 | 11/2001 |
| EP | 1 197 208 | 4/2002 |
| EP | 1 310 517 | 5/2003 |
| GB | 2 145 422 | 3/1985 |
| JP | 7-278277 | 10/1995 |
| JP | 11-269094 | 10/1999 |
| JP | 2000-238051 | 8/2000 |
| WO | 99/36099 | 7/1999 |
| WO | 00/35990 | 6/2000 |
| WO | 01/05380 | 1/2001 |
| WO | 02/12369 | 2/2002 |

OTHER PUBLICATIONS

Notice of Opposition to European Patent No. 1310517 dated Apr. 6, 2006 filed by MediGene AG and represented by Isenbruck et al. of Munchen, Germany, including Facts and Evidence Supporting Opposition, pp. 1-21.
Expert Opinion of Prof. Dr. Claus D. Eisenbach supporting Opponent MediGene AG in Opposition against European Patent No. 1310517, dated Apr. 6, 2006, labelled Exhibit D3, pp. 1-6, Tables 1-2, Figs. 1a-4 and Curriculum Vitae of pp. 1-29 (Eisenbach II).
Notice of Opposition to European Patent No. 1310517 dated Jan. 7, 2007 filed by QLT USA Inc. and represented by Mewburn Ellis LLP of London, England, including Statement of Grounds of Opposition, pp. 1-73.
Expert Opinion of Prof. Dr. Claus D. Eisenbach supporting Opponent QLT USA Inc. in Opposition against European Patent No. 1310517, dated Jan. 2, 2007, labelled Exhibit 3, pp. 1-9, Tables 1a-3b, Figs. 1a-3b and publication (Eisenbach III).
Expert Opinion of Prof. Dr. Claus D. Eisenbach supporting Opponent QLT USA Inc. in Opposition against European Patent No. 1310517, dated Jan. 2, 2007, labelled Exhibit 4, pp. 1-11, Tables 1-2b, Figs. 1a-1b and attached publications (Eisenbach IV).
Response by Patent Owners dated Dec. 7, 2007 to Notice of Oppositions against European Patent No. 1310517 filed by Astellas Pharma, MediGene AG and QLT USA Inc., represented by Lederer & Keller, Munchen, Germany, pp. 1-21, including attachment correlating all references cited in each of the three Oppositions and Exhibits D20, D21, D22, D23 and D24.
Notice of Opposition to European Patent No. 1330293 dated May 18, 2006 filed by Astellas Pharma Europe Ltd. and represented by Hoffmann-Elite of Munchen, Germany, including Facts and Evidence Supporting Opposition, pp. 1-32 together with papers from Notice of Opposition against European Patent No. 1310517.
Notice of Opposition to European Patent No. 1330293 dated May 18, 2006 filed by MediGene AG and represented by Isenbruck et al. of Munchen, Germany, including Facts and Evidence Supporting Opposition, pp. 1-20.
Notice of Opposition to European Patent No. 1330293 dated Feb. 16, 2007 filed by QLT USA Inc. and represented by Mewburn Ellis LLP of London, England, including Statement of Grounds of Opposition, pp. 1-101 and including Annex 1 pp. 1-5.
Response by Patent Owners dated Dec. 7, 2007 to Notice of Oppositions against European Patent No. 1330293 filed by Astellas Pharma, MediGene AG and QLT USA Inc., represented by Lederer & Keller, Munchen, Germany, pp. 1-26, including Exhibits D30, D31, D32, D33, D34 and D35.
"Pschyrembel Klinisches Worterbuch", (1994), 257, Ed., de Gruyter, Berlin, New York, Sections "GnRH" and "GnRH-Agonisten".
The Merck Index, 11$^{th}$ Ed., 1989, "Goserelin", Entry 4433, p. 711.
The Merck Index, 11$^{th}$ Ed., 1989, "Triptorelin", Entry 9662, pp. 1533-1534.
T. Taguchi et al., "Long-Term Clinical Study on TAP-144-SR, An LH-RH Agonist Depot Formulation, in Premenopausal Patients with Advanced or Recurrent Breast Cancer. TAP-144-SR Breast Cancer Study Group", Gan To Kagaku Ryoho, vol. 22, No. 4, pp. 495-508, Mar. 1995 with English language abstract.
"Rote Liste" (2000), Sections "Enantone", "Kryptocur", "Lutrelef".
"The Merck Index" (2001), 13. Ed., Section "Leuprolide".
T. G. Park, "Degradation of Poly(D,L-Lactic Acid) Microspheres: Effect of Molecular Weight", Journal of Controlled Release, vol. 30, No. 2, pp. 161-173, May 30, 1994.
Y. Aso et al., "Effect of Temperature on Mechanisms of Drug Release and Matrix Degradation of Poly(D,L-Lactide) Microspheres", Journal of Controlled Release, vol. 31, No. 1, pp. 33-39, Aug. 31, 1994.
J. Woodland et al., "Long-Acting Delivery Systems for Narcotic Antagonists", J. Med. Chem., vol. 16, pp. 897-901, 1973.
R. K. Kulkarni et al., "Biodegradable Poly(lactic acid) Polymers", J. Biomed. Mater. Res., vol. 5, pp. 169-181, 1971.
D. Braun et al., "Practical Training in Macromolecular Organic Chemistry", pp. 57-59, 1966 (with English translation).
J. Falbe et al., "Rompp Chemistry Lexicon", Ed. 9, vol. 4, pp. 3107-3108, 1991 Section "Oligomere" (with English translation).
D. L. Wise et al., "Encyclopedic Handbook of Biomaterials and Bioengineering", Synthesis and Properties of Biodegradable Lactic/Glycolic Acid Polymers, Part A; Materials, vol. 2, pp. 1015-1049, Marcel Dekker, NY, 1995.
T. D. Brock, "Membrane Filtration", A Users Guide and Reference Manual, Chapter 13. 5 Membranes used in Ultrafiltration, pp. 290-291, Springer-Verlag, Berlin, Heidelberg, NY, 1983.
C. Pitt et al., "Sustained Drug Delivery System. I. The Permeability of Poly(ε-Caprolactone), Poly(DL-Lactic Acid), and Their Copolymers", Journal of Biomedical Materials Research, vol. 13, pp. 497-507, 1979.
R. Miller et al., "Degradation Rates of Oral Resorbable Implants (Polylactates and Polyglycolates): Rate Modification with Changes in PLA/PGA Copolymer Ratios", Journal of Biomedical Materials Research, vol. 11, No. 5, pp. 711-719, Sep. 1977.
L. R. Beck et al., "Systemic and Local Delivery of Contraceptive Steroids Using Biodegradable Microcapsules", Progress in Contraceptive Delivery Systems, vol. 1, pp. 63-81, 1980.
A. Schindler et al., "Biodegradable Polymers for Sustained Drug Delivery", Contemporary Topics in Polymer Science, vol. 2, (Pearce and Schaefgen eds.)., pp. 251-286, Plenum Publishing Corp., 1977.
K. Suzuki et al., Microencapsulation and Dissolution Properties of a Neuroleptic in a Biodegradable Polymer, Poly(d,l-lactide), Journal of Pharmaceutical Sciences, vol. 74, No. 1, pp. 21-25, Jan. 1985.
M. Vert et al., "Stereoregular Bioresorbable Polyesters for Orthopedic Surgery", Makromol. Chem. Supp., vol. 5, pp. 30-41, 1981.
M. Vert et al., "Bioresorbable Plastic Materials for Bone Surgery", Macromolecular Biomaterials, Chapter 6, pp. 119-142, 1984.
J. Ruiz et al., "Influence of Average Molecular Weights of Poly(DL-Lactic Acid-Co-Glycolic Acid) Copolymers 50/50 on Phase Separation and in Vitro Drug Release from Microspheres", Pharmaceutical Research, vol. 7, No. 9, pp. 928-934, 1990.
B. Schartel et al., "Dielectric and Thermodynamic Properties of Biodegradable Poly(D,L-Lactide-Co-Glycolide) and the Effect on the Micro-Encapsulation and Release of Captopril", J. Microencapsulation, vol. 14, No. 4, pp. 475-488, 1997.
B. Bittner et al., "Bovine Serum Albumin Loaded Poly(Lactide-Co-Glycolide) Microspheres: The Influence of Polymer Purity on Particle Characteristics", J. Microencapsulation, vol. 15, No. 4, pp. 495-514, 1998.
E. Collins et al.,"B. Isolation and Purification of Polymer", Experiments in Polymer Science, pp. 62-69, published 1973 by John Wiley & Sons.

* cited by examiner ns of Ser. No. 11/348,464
LACTIC ACID POLYMER AND PROCESS FOR PRODUCING THE SAME This is a continuation application of Ser. No. 11/348,464 filed Feb. 7, 2006, now abandoned which is a divisional application of Ser. No. 10/344,131, filed Apr. 3, 2003, now issued as U.S. Pat. No. 7,019,106, which is a U.S. national stage of International Application No. PCT/JP01/06721 filed Aug. 6, 2001.

TECHNICAL FIELD

The present invention relates to a biodegradable polymer useful as a matrix for pharmaceutical preparations.

BACKGROUND ART

Biodegradable polymers having a sustained-release property are useful as matrices for microcapsules, etc. to be employed for encapsulating physiologically active substances. As such biodegradable polymers, there are known, for instance, polylactic acid and a copolymer of lactic acid and glycolic acid (e.g. JP-A-11/269,094).

These biodegradable polymers are used just as produced by conventional synthetic procedures. However, it has been found that such polymers produced by ring-opening polymerization are small in the terminal carboxyl group content and have poor utilization as sustained-release matrices. Because of this reason, attempt has been made to subject biodegradable polymers of high molecular weight to hydrolysis for making their weight-average molecular weights suitable and then use as a matrix for sustained-release preparations. The polymers obtained by hydrolysis and subsequent water washing are, however, apt to cause initial burst and therefore not suitable for sustained-release matrices, even when said polymers have proper weight-average molecular weights and terminal carboxyl group contents. Further improvement is thus demanded.

DISCLOSURE OF INVENTION (Technical Problem(s) to be Solved by Invention)

Under the above circumstances, the present invention has been made aiming at providing a lactic acid polymer useful as a matrix for sustained-release preparations which can fully prevent the initial excessive release (initial burst) of a physiologically active substance from the microcapsules encapsulating a physiologically active substance and keep a stable release rate of the physiologically active substance over a long period of time.

(Solution of Technical Problem(s))

As a result of the extensive study, it has been found that a lactic acid polymer obtained by hydrolysis, i.e. a lactic acid polymer which is decreased in the content of polymeric materials of low molecular weights, particularly having not more than 5,000 in weight-average molecular weight, is hard to cause the initial burst and is suitable as a matrix for sustained-release preparations. On the basis of this finding, the present invention has been completed.

According to the present invention, there is provided a process for producing a lactic acid polymer of 15,000 to 50,000 in weight-average molecular weight, the content of polymeric materials having not more than about 5,000 in weight-average molecular weight therein being not more than about 5% by weight, which comprises hydrolyzing a high molecular weight lactic acid polymer, placing the resultant solution containing the hydrolyzed product under a condition capable of making the produced objective lactic acid polymer precipitated, separating the precipitated lactic acid polymer and collecting them.

There is also provided a process for removing polymeric materials of not more than about 5,000 in weight-average molecular weight from a high molecular weight lactic acid polymer, which comprises hydrolyzing the high molecular weight lactic acid polymer, placing the resultant solution containing the hydrolyzed product under a condition capable of making the produced objective lactic acid polymer precipitated, separating the precipitated lactic acid polymer and collecting them.

There is further provided a lactic acid polymer of 15,000 to 50,000 in weight-average molecular weight, the content of polymeric materials having not more than 5,000 in weight-average molecular weight therein being not more than about 5% by weight.

There are furthermore provided the use of the lactic acid polymer as stated above as a matrix for sustained-release preparations and a matrix for sustained-release preparations comprising the lactic acid polymer as stated above.

(Better Effect in Comparison with Prior Art)

In comparison with conventional lactic acid polymers used as biodegradable polymers for sustained-release preparations, the lactic acid polymer of this invention has a smaller content of polymeric materials of low molecular weight, particularly having not more than 5,000 in weight-average molecular weight, and therefore hardly causes initial excessive release.

BEST MODE FOR PRACTICING INVENTION

The lactic acid polymer of this invention may comprise a homopolymer of lactic acid or a copolymer of lactic acid with any other monomer (e.g., glycolic acid). Such homopolymer or copolymer has usually a content of polymeric materials having not more than 5,000 in weight-average molecular weight being not more than about 5% by weight, preferably a content of polymeric materials having not, more than 5,000 in weight-average molecular weight being not more than about 5% by weight with a content of polymeric materials having not more than 3,000 in weight-average molecular weight being not more than about 1.5% by weight, more preferably a content of polymeric materials having not more than 5,000 in weight-average molecular weight being not more than about 5% by weight with a content of polymeric materials having not more than 3,000 in weight-average molecular weight being not more than about 1.5% by weight and a content of polymeric materials having not more than 1,000 in weight-average molecular weight being not more than about 0.1% by weight.

The lactic acid polymer of the present invention has usually 15,000 to 50,000, preferably 15,000 to 30,000, more preferably 20,000 to 25,000 in weight-average molecular weight.

The high molecular weight lactic acid polymer to be used as a starting material for preparation of the objective lactic acid polymer may be commercially available or obtained by polymerization in a conventional manner and has usually a weight-average molecular weight of 15,000 to 500,000, preferably 30,000 to 100,000. Conventional polymerization methods include polycondensation of lactic acid, if necessary, with glycolic acid, ring-opening polymerization of lactide, if necessary, with glycolide in the presence of a catalyst such as Lewis acid (e.g., diethyl zinc, triethyl aluminum, stannous octanoate) or a metallic salt, ring-opening polymerization of lactide in the same manner as above except for in the presence of a hydroxycarboxylic acid derivative wherein the carboxy group is protected (e.g., International Publication No. WO 00/35990), ring-opening polymerization of lactide using a catalyst under heating (e.g., J. Med. Chem., 16, 897 (1973)), copolymerization of lactide with glycolide, etc.

As the polymerization mode, there are bulk polymerization where lactide or the like is subjected to polymerization as a melt, solution polymerization where lactide or the like is subjected to polymerization as a solution in an appropriate solvent, etc. In this invention, it is favorable from the viewpoint of industrial production to use a high molecular weight lactic acid polymer obtained by solution polymerization as the starting material for production of the objective lactic acid polymer.

The solvent to be used in solution polymerization for dissolving lactide may be, for instance, aromatic hydrocarbons (e.g., benzene, toluene, xylene), decalin, dimethylformamide or the like.

In order to hydrolyze the thus obtained high molecular weight lactic acid polymer, there may be adopted a per se conventional hydrolyzing procedure. For instance, the high molecular weight lactic acid polymer is dissolved in an appropriate solvent, and water and, if necessary, an acid are added thereto, followed by reaction.

The solvent which dissolves the high molecular weight lactic acid polymer may be any one capable of dissolving one part by weight of said polymer in not more than 10 parts by weight. Specific examples are halogenated hydrocarbons (e.g., chloroform, dichloromethane), aromatic hydrocarbons (e.g., toluene, o-xylene, m-xylene, p-xylene), cyclic ethers (e.g., tetrahydrofuran), acetone, N,N-dimethylformamide, etc. When the solvent used on polymerization for production of the high molecular weight lactic acid polymer is the one also usable for hydrolysis of such polymer, the polymerization and the hydrolysis may be carried out successively without isolating the polymerized high molecular weight lactic acid polymer.

The amount of the solvent which dissolves the high molecular weight lactic acid polymer is usually 0.1 to 100 times in weight, preferably 1 to 10 times in weight of said polymer as the solute. The amount of water to be added is usually 0.001 to 1 part by weight, preferably 0.01 to 0.1 part by weight to one part by weight of the high molecular weight lactic acid polymer.

Examples of the acid which may be added when needed include inorganic acids (e.g., hydrochloric acid, sulfuric acid, nitric acid), organic acids (e.g., lactic acid, acetic acid, trifluoroacetic acid), etc., among which lactic acid is preferred. The amount of the acid to be added is usually not more than 10 parts by weight, preferably 0.1 to 1 part by weight to one part by weight of the high molecular weight lactic acid polymer.

The reaction temperature for hydrolysis is usually 0 to 150° C., preferably 20 to 80° C. The reaction time for hydrolysis is varied with the weight-average molecular weight of the high molecular weight lactic acid polymer and the reaction temperature and is usually 10 minutes to 100 hours, preferably 1 to 20 hours.

Completion of the hydrolysis may be determined on the basis of the weight-average molecular weight of the hydrolyzed product. Namely, sampling of the hydrolyzed product is done at a suitable interval during the hydrolysis, and the weight-average molecular weight of the hydrolyzed product as sampled is measured by gel permeation chromatography (GPC). When the weight-average molecular weight is confirmed to be about 15,000 to 50,000, preferably about 15,000 to 30,000, more preferably about 20,000 to 25,000, the hydrolysis is terminated.

The method for precipitating the objective lactic acid polymer from the solution containing the hydrolyzed product obtained by hydrolyzing the high molecular weight lactic acid polymer includes, for instance, a method for contacting a solution containing the hydrolyzed product with a solvent capable of precipitating the objective lactic acid polymer present therein.

The solution containing the hydrolyzed product is preferred to the one wherein the lactic acid polymer of 15,000 to 50,000, preferably 15,000 to 30,000, more preferably 20,000 to 25,000 in weight-average molecular weight is dissolved in a solvent such as halogenated hydrocarbons (e.g., chloroform, dichlormethane), aromatic hydrocarbons (e.g., toluene, o-xylene, m-xylene, p-xylene), cyclic ethers (e.g., tetrahydrofuran), acetone or N,N-dimethylformamide, in a concentration of about 10 to 50% by weight.

The solvent for precipitating the objective lactic acid polymer in the solution containing the hydrolyzed product may be, for example, alcohols (e.g., methanol, ethanol), acyclic ethers (e.g., isopropyl ether), aliphatic hydrocarbons (e.g., hexane), water or the like.

The amount of the solvent capable of precipitating the objective lactic acid polymer is usually 0.1 to 100 parts by weight, preferably 1 to 10 parts by weight to one part by weight of the liquid medium in the solution containing the hydrolyzed product.

A preferred example of the combination of the liquid medium and the solvent as well as their proportion is the combination of using of 2 to 10 parts by weight of isopropyl ether as the solvent for reducing the solubility of the objective lactic acid polymer to one part by weight of dichloromethane which is used as the liquid medium in the solution containing the hydrolyzed product in a proportion of 1 to 5 parts by weight to one part by weight of the solute.

On the contact of the solvent capable of precipitating the objective lactic acid polymer with the solution containing the hydrolyzed product, the temperature of said solvent is usually −20 to 60° C., preferably 0 to 40° C., and the temperature of said solution is usually 0 to 40° C., preferably 10 to 30° C.

As the procedure for contacting the solvent capable of precipitating the objective lactic acid with the solution containing the hydrolyzed product, there are addition of said solution to said solvent at one time, dropwise addition of said solution to said solvent, addition of said solvent to said solution at one time, dropwise addition of said solvent to said solution, etc.

The lactic acid polymer of the invention thus obtained has a favorable terminal carboxyl group content suitable as a matrix for sustained-release preparations and can be used as such matrix. When the lactic acid polymer is used as a matrix for sustained-release, preparations, a physiologically active substance to be encapsulated therein has no particular limitation insofar as it is pharmacologically effective. The physiologically active substance may be a peptidic compound or a non-peptidic compound. As the non-peptidic compound, there are exemplified an agonist, an antagonist, a compound having an enzyme inhibition activity, etc.

A peptidic compound is preferred, for instance, to be a physiologically active one, especially having a molecular weight of about 300 to 40,000, preferably of about 400 to 30,000, more preferably of about 500 to 25,000, most preferably of about 500 to 20,000.

Examples of the physiologically active peptide include luteinizing hormone releasing hormone (LH-RH), insulin, somatostatin, growth hormone, growth hormone releasing hormone (GH-RH), prolactin, erythropoietin, adrenocortical hormone, melanocyte stimulation hormone, thyroid hormone releasing hormone, thyroid stimulating hormone, luteinizing hormone, follicle stimulating hormone, vasopressin, oxytocin, calcitonin, gastrin, secretin, pancreozymin, cholecystokinin, angiotensin, human placenta lactogen, human choriogonadotropin, enkephalin, endorphin, kyotorphin, tuftsin, thymopoietin, thymosin, thymothymulin, thymus humoral factor, thymic factor in blood, tumor necrosis factor, colony inducing factor, motilin, dynorphin, bombesin, neurotensin, cerulein, bradykinin, atrial natriuretic factor, nerve growth factor, cell proliferation factor, neurotrophic factor, endothelin antagonistic peptide, etc., their derivatives, their fragments and derivatives thereof, etc.

The physiologically active peptide may be in a free form or a pharmacologically acceptable salt form. Examples of the salt are, in case of the physiologically active peptide having a basic group such as amino, salts with inorganic acids (e.g., carbonic acid, bicarbonic acid, hydrochloric acid, sulfuric acid, nitric acid, boric acid), salts with organic acids (e.g., succinic acid, acetic acid, propionic acid, trifluoroacetic acid), etc. In case of the physiologically active peptide having an acidic group such as carboxyl, examples of the salt are salts with inorganic bases such as alkali metals (e.g., sodium, potassium) and alkaline earth metals (e.g., calcium, magnesium), salts with organic bases such as organic amines (e.g., trietylamine) and basic amino acids (e.g., arginine). The physiologically active peptide may also form a metal complex such as copper complex or zinc complex.

Among the physiologically active peptides as exemplified above, preferred are LH-RH derivatives and their salts which are effective in treatment of sexual hormone-dependent diseases such as prostatic cancer, benign prostatic hyperplasia, endometriosis, fibroid, precocious puberty and breast cancer or useful for contraception. Specific examples are leuprorelin, buserelin, goserelin, tryptorelin, nafarelin, histrelin, deslorelin, meterelin, gonadorelin, etc.

The sustained-release preparation prepared by the use of the lactic acid polymer of the invention as a matrix may contain, in addition to the physiologically active substance, a surfactant such as Tween80 (manufactured by Atlas Powder) and HCO-60 (manufactured by Nikko Chemicals), a polysaccharide such as carboxymethylcellulose, sodium alginate and sodium hyaluronate, a dispersant such as protamine sulfate and polyethyleneglycol 400, a preservative such as methylparaben and propylparaben, an isotonic agent such as sodium chloride, mannitol, sorbitol and glucose, an oil or fat such as sesame oil and corn oil, a phospholipid such as lecithin, an excipient such as lactose, corn starch, mannitol and cellulose, a dextrin binding agent such as sucrose, acacia, methylcellulose and carboxymethylcellulose, a disintegrant such as carboxymethylcellulose calcium, a drug retaining agent such as gelatin, hydroxynaphthoic acid and salicylic acid, etc.

The sustained-release preparation comprising the lactic acid polymer of the invention as the biodegradable polymer may be prepared by a per se conventional method such as underwater drying method, phase separation method, spray drying method or any other method similar thereto.

Preparation of microcapsules (hereinafter sometimes referred to as "microspheres") as an example of the sustained-release preparation will be explained below. At any step or stage in the preparation method, any drug retaining agent (e.g., gelatin, hydroxynaphthoic acid, salicylic acid) may be optionally used in a per se conventional manner.

(I) In-Water-Drying Method
(i) O/W Method

In this method, there is first prepared a solution of the lactic acid polymer of the present invention (hereinafter sometimes referred to as "biodegradable polymer") in an organic solvent.

The organic solvent usable for manufacture of the sustained-release preparation according to the invention is preferred to have a boiling point of 120° C. or lower.

As the organic solvent, there can be used, for example, halogenated hydrocarbons (e.g., dichloromethane, chloroform, dichloroethane, trichloroethane, carbon tetrachloride), ethers (e.g., ethyl ether, isopropyl ether), fatty acid esters (e.g., ethyl acetate, butyl acetate), aromatic hydrocarbons (e.g., benzene, toluene, xylene), alcohols (e.g., ethanol, methanol), acetonitrile, etc. Among them, the use of halogenated hydrocarbons, particularly dichloromethane, is favorable. These solvents may be used in a mixture in an appropriate proportion, and in this case, mixtures of halogenated hydrocarbons and alcohols, particularly a mixture of dichloromethane and ethanol, are preferred.

The concentration of the biodegradable polymer of the invention in the solution is varied with the molecular weight of the biodegradable polymer and the kind of the organic solvent. When, for instance, dichloromethane is used as the organic solvent, the concentration may be usually about 0.5 to 70% by weight, preferably about 1 to 60% by weight, more preferably about 2 to 50% by weight. In case of using a mixture of dichloromethane and ethanol as the organic solvent, ethanol may be employed generally in an amount of about 0.01 to 50% (v/v), preferably of about 0.05 to 40% (v/v), more preferably of about 0.1 to 30% (v/v) based on the total amount of them.

To the thus prepared organic solution of the biodegradable polymer, a physiologically active substance is added to dissolve or disperse. The physiologically active substance is used in such amount as the weight ratio of the physiologically active substance and the biodegradable polymer being usually not more than about 1/1, preferably not more than about 1/2.

Then, the organic solution comprising the physiologically active substance or its salt and the biodegradable polymer is added to a water phase to make an O(oil phase)/W(water phase) emulsion, followed by evaporation of the solvent in the oil phase to give microcapsules. The volume of the water phase is usually about 1 to 10,000 times, preferably about 5 to 50,000 times, more preferably about 10 to 2,000 times that of the oil phase.

When desired, an emulsifier may be incorporated into the water phase. In general, the emulsifier may be anyone capable of forming a stable O/W emulsion. Specific examples of the emulsifier usable are anionic surfactants (e.g., sodium oleate, sodium stearate, sodium lauryl sulfate), non-ionic surfactants (e.g., polyoxyethylene sorbitan fatty acid esters [Tween 80, Tween 60 manufactured by Atlas Powder], polyoxyethylene castor oil derivatives [HCO-60, HCO-50 manufactured by Nikko Chemicals]), polyvinyl pyrrolidone, polyvinyl alcohol, carboxymethyl cellulose, lecithin, gelatin, hyaluronic acid, etc. These emulsifiers may be used alone or in combination. When used, the concentration of the emulsifier is preferred to be about 0.01 to 10% by weight, particularly about 0.05 to 5% by weight.

An osmotic pressure regulating agent may be also incorporated into the water phase. As the osmotic pressure regulating agent, there may be used anyone capable of showing an osmotic pressure in aqueous solution. As the osmotic pressure regulating agent, there are exemplified polyvalent alcohols, monovalent alcohols, monosaccharides, disaccharides, oligosaccharide and amino acids, and their derivatives.

Examples of the polyvalent alcohols are trivalent alcohols (e.g., glycerol), pentavalent alcohols (e.g., arabitol, xylitol, adonitol), hexavalent alcohols (e.g., mannitol, sorbitol, dulcitol), etc. Of these, the use of hexavalent alcohols, particularly of mannitol, is preferred. Examples of the monovalent alcohols are methanol, ethanol, isopropanol, etc., among which ethanol is preferable. Examples of the monosaccharides are pentoses (e.g., arabinose, xylose, ribose, 2-deoxyribose), hexoses (e.g., glucose, fructose, galactose, mannose, sorbose, rhamnose, fucose), etc. among which the use of hexoses is preferred. As the oligosaccharides, there may be used, for example, trisaccharides (e.g., maltotriose, raffinose), tetrasaccharides (e.g., stachyose), of which trisaccharides are favorably used.

The derivatives of monosaccharides, disaccharides and oligosaccharides include, for example, glucosamine, galactosamine, glucuronic acid, galacturonic acid, etc. The amino acids are usable insofar as those are of L-configuration, and the specific examples are glycine, leucine arginine, etc., of which L-arginine is preferred.

Said osmotic pressure regulating agents may be used alone or in combination. When used, the concentration may be such as affording the osmotic pressure of the water phase being about 1/50 to 5 folds, preferably about 1/25 to 3 folds that of physiological saline.

Removal of the organic solvent may be accomplished by a per se conventional procedure or any other procedure similar thereto. For instance, evaporation of the organic solvent is carried out under atmospheric pressure or gradually reduced pressure while stirring with a propeller type agitator or a magnetic stirrer or under control of the degree of vacuum by the use of a rotary evaporator.

The thus prepared microcapsules are collected by centrifugation or filtration, washed with distilled water several times repeatedly to eliminate the physiologically active substance, the emulsifier and any other material attached onto the surfaces of the microcapsules and redispersed into distilled water, followed by freeze drying.

During the manufacture, an anti-cohesion agent may be added to the microcapsules for prevention of the cohesion between or among them. Examples of the anti-cohesion agent are water-soluble polysaccharides (e.g., mannitol, lactose, glucose, starches such as corn starch), amino acids (e.g., glycine), proteins (e.g., fibrin, collagen), etc. Among them, mannitol is preferred.

After the freeze drying, the moisture and the organic solvent in the microcapsules may be optionally eliminated by heating under a condition not causing the fusion if the microemulsions. Heating is preferably carried out at a temperature slightly higher than the mid-point glass transition temperature of the biodegradable polymer as determined by the use of a differential scanning calorimeter under a temperature elevation rate of 10 to 20° C./min. More preferably, heating is effected at a temperature of from the mid-point glass transition temperature of the biodegradable polymer to about 3° C. higher temperature than said mid-point glass transition temperature. In case of the lactic acid/glycolic acid copolymer being used as the biodegradable polymer, it is particularly preferred to heat at a temperature between the mid-point glass transition temperature of said copolymer and 10° C. higher than such mid-point glass transition temperature, more preferably between said mid-point glass transition temperature and 5° C. higher than such mid-point glass transition temperature.

The heating time is varied with the amount of the microcapsules and normally about 12 to 168 hours, preferably about 24 to 120 hours, more preferably about 48 to 96 hours after the microcapsules themselves reach a pre-determined temperature.

Any particular restriction is present on the heating procedure insofar as the collection of the microcapsules is uniformly heated. The heating is thus carried out, for instance, by heat drying in a thermostat bath, a fluidized bed tank, a mobile bath or a kiln or by heat drying with microwave. Especially, heating dry in a thermostat bath is preferable.

(ii) W/O/W Method

In this method, a solution of the biodegradable polymer of the invention in an organic solvent is first prepared.

As the organic solvent, there may be used, for example, halogenated hydrocarbons (e.g., dichloromethane, chloroform, dichloroethane, trichloroethane, carbon tetrachloride), ethers (e.g., ethyl ether, isopropyl ether), fatty acid esters (e.g., ethyl acetate, butyl acetate), aromatic hydrocarbons (e.g., benzene, toluene, xylene), alcohols (e.g., ethanol, methanol), acetonitrile, etc. Among them, the use of halogenated hydrocarbons, particularly dichloromethane, is favorable. These solvents may be used in a mixture in an appropriate proportion, and in this case, mixtures of halogenated hydrocarbons and alcohols, particularly a mixture of dichloromethane and ethanol, are preferred.

The concentration of the biodegradable polymer in the organic solution is varied with the molecular weight of the biodegradable polymer and the kind of the organic solvent. When, for instance, dichloromethane is used as the organic solvent, the concentration may be usually about 0.5 to 70% by weight, preferably about 1 to 60% by weight, more preferably about 2 to 50% by weight.

To the thus prepared organic solution of the biodegradable polymer (oil phase), a solution of a physiologically active substance or its salt (using water or a mixture of water and an alcohol (e.g., methanol, ethanol) as a solvent) is added. The resultant mixture is emulsified by a per se conventional procedure with a homogenizer or ultrasonics to form a W/O emulsion.

Then, the thus obtained W/O emulsion comprising the physiologically active substance and the biodegradable polymer is added to a water phase to form a W(inner water phase)/O(oil phase)/W(outer water phase) emulsion, followed by evaporation of the solvent in the oil phase to make microcapsules. The volume of the outer water phase is generally about 1 to 10,000 parts, preferably about 5 to 50,000 parts, more preferably about 10 to 2,000 parts to one part of the oil phase.

The emulsifier and the osmotic pressure regulating agent which may be added optionally to said outer water phase and the subsequent procedure for preparation are the same as stated in the foregoing paragraph (I)(i).

(II) Phase Separation Method

In case of manufacture of the microcapsules by this method, a coacervation agent is gradually added to the organic solution comprising the physiologically active substance and the biodegradable polymer as stated in the in-water-drying method under the foregoing paragraph (I) while stirring to precipitate and solidify the microcapsules. The coacervation agent is employed in an amount of usually about 0.01 to 1,000 times, preferably about 0.05 to 500 times, most preferably about 0.1 to 200 times of the volume of the oil phase.

As to the coacervation agent, there is no particular limitation insofar as it is a high molecular weight compound, a mineral oil, a plant oil our the like which is miscible with an organic solvent and does not dissolve the degradable polymer of the invention therein. Specific examples are silicone oil, sesame oil, soybean oil, corn oil, cottonseed oil, coconut oil, linseed oil, mineral oil, n-hexane, n-heptane, etc. These may be used alone or in combination.

The thus prepared microcapsules are collected, washed with heptane or the like repeatedly to remove the coacervation agent, etc. other than the physiologically active substance and the biodegradable polymer of this invention, followed by drying under reduced pressure. Alternatively, in the same manner as stated in the in-water-drying method under the foregoing paragraph (I), the microcapsules are washed and freeze dried, if necessary, followed by heat drying.

(III) Spray Drying Method

For manufacture of the microcapsules by this method, the organic solution or dispersion comprising the physiologically active substance and the biodegradable polymer as stated in the in-water-drying, method under the foregoing paragraph (I) is sprayed by the aid of a nozzle into the drying chamber of a spray dryer so as to evaporate the organic solvent in the atomized droplets within a very short time to make microcapsules. Said nozzle may be of two flow nozzle type, pressure nozzle type, rotary disk form or the like. When necessitated, washing and freeze drying, optionally followed by heat drying may be effected in the same manner as stated for the in-water-drying method under the foregoing (I).

As an example of the preparation form other than the microcapsules, there are microparticles, which may be prepared by subjecting the organic solution or dispersion comprising the physiologically active substance and the biodegradable polymer as stated in the in-water-drying method under the foregoing paragraph (I) to evaporation of the organic solvent and water therein under the control of the degree of vacuum, for instance, using a rotary evaporator to dryness, followed by pulverization by the aid of a jet mill or the like to give fine particles, i.e. microparticles. When desired, the thus obtained microparticles may be further subjected to washing and freeze drying, optionally followed by heat drying in the same manner as stated in the underwater drying method under the foregoing paragraph (I).

The microcapsules or microparticles as obtained above can attain a favorable release of the physiologically active substance corresponding to the decomposition rate of the biodegradable polymer used therein.

The sustained-release composition obtained as above may be administered as such or after formulation into any appropriate preparation form using the same as the starting material, said preparation form including an injection or implant for intramuscular, subcutaneous or intraorgan route, a transmucous agent through nasal cavity, rectum, uterus or the like, an oral agent such as a solid preparation (e.g., capsules such as soft gelatin capsules and hard gelatin capsules, granules, powders) and a liquid preparation (e.g., syrup, emulsion, suspension), etc.

For example, the sustained-release composition can be prepared as a sustained-release injection by admixing said composition with water and a dispersant (e.g., a surfactant such as Tween80 and HCO-60, a polysaccharide such as sodium hyaluronate, carboxymethylcellulose and sodium alginate), a preservative (e.g., methylparaben, propylparaben), an isotonizing agent (e.g., sodium chloride, mannitol, sorbitol, glucose, proline) or the like to make an aqueous suspension or by dispersing said composition into a plant oil (e.g. sesame oil, corn oil) or the like to make an oily suspension. The aqueous or oily suspension is practically usable as a sustained-release injection.

The particle size in the sustained-release composition may be within a range capable of passing through a needle for injection, which is usually about 0.1 to 300 μm, preferably about 0.5 to 150 μm, more preferably about 1 to 100 μm in average particle size. The average particle size can be determined by a per se conventional procedure using an apparatus for measurement of particle size distribution with laser analysis (SALD2000A: manufactured by Shimadzu Seisakusho).

In order to make a sterile preparation using the sustained-release composition obtained with the lactic acid polymer of the present invention as a matrix, the entire stages or steps for preparation may be sterilized. Alternatively, sterilization with γ-ray or incorporation of an antiseptic agent may be applied. In any event, there is no particular limitation for sterilization.

The sustained-release composition obtained by using the lactic acid polymer of the present invention as a matrix is low in toxicity and can be used as a safe drug for mammals (e.g., human beings cows, pigs, dogs, cats, mice, rats, rabbits).

The sustained-release composition can be used as an agent for prevention and treatment of various diseases depending upon the physiologically active substance included therein. When, for instance, the physiologically active substance is an LH-RH derivative, the composition can be used as an agent for prevention and treatment of sexual hormone-dependent diseases, especially sexual hormone-dependent cancers (e.g., prostatic cancer, uterus cancer, breast cancer, pituitary tumor), benign prostatic hyperplasia, endometriosis, fibroid, precocious puberty, dysmenorrhea, amenorrhea, premenstrual syndrome, multilocular ovarian syndrome, etc., or as an agent for contraception (or, in case of utilizing the rebound effect after interruption of the administration, for prevention and treatment of infertility). The composition can be also used as an agent for prevention and treatment of benign or malignant tumor which is not dependent on sexual hormone but sensitive to LH-RH.

The dosage amount of the sustained-release composition may correspond to the effective dose of the physiologically active substance as the active ingredient therein, although it is varied with the kind and content of the physiologically active substance, the formulation, the duration for releasing the physiologically active substance, the symptom of the disease, the species of the animal, etc. A single dosage amount of the physiologically active substance may be appropriately chosen from a range of about 0.01 to 10 mg/kg bodyweight, preferably of about 0.05 to 0.5 mg/kg bodyweight for a human adult when the sustained-release preparation is the one covering 6 months.

A single dosage of the sustained-release composition may be appropriately selected from a range of about 0.05 to 50 mg/kg bodyweight more preferably a range of about 0.1 to 30 mg/kg bodyweight for a human adult.

The frequency of administration can be suitably selected from once for several weeks, once for one month, once for several months (e.g., 3 months, 4 months, 6 months), etc. taking into consideration the kind and content of the physiologically active substance as an active ingredient, the formulation, the duration for releasing the physiologically active substance, the symptom of the disease, the species of the animal, etc.

As stated above, the lactic acid polymer of the present invention is useful as a matrix for sustained-release preparations containing a physiologically active substance and fully prevent the initial excessive release and retaining a stable release rate of the physiologically active substance over a long period of time, for instance, six months or more.

The present invention will be hereinafter explained in details by way of examples but these examples should not be understood to limit the scope of the present invention thereto.

EXAMPLES

In the following descriptions, the weight-average molecular weight and the polymer content are respectively the one in terms of polystyrene measured by gel permeation chromatography (GPC) using monodisperse polystyrene as the certified reference material and the one calculated therefrom. All the measurements were made by a high performance GPC apparatus (manufactured by Tosoh Corp.; HLC-8120GPC) using SuperH4000×2 and SuperH2000 (both manufactured by Tosoh Corp.) as the column and tetrahydrofuran at a flow rate of 0.6 ml/min as the mobile phase. Detection was effected with differential refractive index.

Production Example 1

Synthesis of the High Molecular Weight Lactic Acid Polymer

To dehydrated xylene (230 ml), 1.0 mol/L diethyl zinc hexane solution (4.1 ml), tert-butyl lactate (1.35 g) and DL-lactide (230 g) were added, and polymerization was carried out at 120 to 130° C. for about 2 hours. After completion of the polymerization, dichloromethane (120 ml) was poured into the reaction mixture, followed by addition of trifluoroacetic acid (230 ml) thereto for deprotecting reaction. After completion of the reaction, dichloromethane (300 ml) was added to the reaction mixture, which was then poured into isopropyl ether (2800 ml) to precipitate high molecular weight lactic acid polymers. The precipitate as the objective product was subjected to reprecipitation repeatedly with dichloromethane/isopropyl ether to give a lactic acid polymer of about 40,000 in weight-average molecular weight.

Reference 1

The polymer obtained in Production Example 1 was dissolved in dichloromethane (600 ml). The resulting solution washed with water to make neutral, and 90% lactic acid aqueous solution (70 g) was added thereto, followed by reaction at 40° C. When the weight-average molecular weight of the polymer dissolved in the reaction mixture reached about 20,000, cooling was made to room temperature, and dichloromethane (600 ml) was added thereto to terminate the reaction. The reaction mixture was washed with water to make neutral, concentrated and dried to give a lactic acid polymer. The terminal carboxyl group content in the lactic acid polymer was about 80 µmol relative to 1 g of the polymer, and the content of the polymer of not more than 5,000 in weight-average molecular weight was 7.29% by weight.

Example 1

The polymer obtained in Production Example 1 was dissolved in dichloromethane (600 ml), and the resulting solution washed with water to make neutral, and 90% lactic acid aqueous solution (70 g) was added thereto followed by reaction at 40° C. When the weight-average molecular weight of the polymer dissolved in the reaction mixture reached about 20,000, cooling was made to room temperature, and dichloromethane (600 ml) was added thereto to terminate the reaction. The reaction mixture was washed with water to make neutral and added dropwise to isopropyl ether (2800 ml) to precipitate the objective lactic acid polymer. The precipitate was collected by decantation and dissolved in dichloromethane (600 ml). The resultant solution was concentrated and dried to give a lactic acid polymer (160 g). The terminal carboxyl group content in the lactic acid polymer was about 70 µmol relative to 1 g of the polymer. The weight-average molecular weight of the high molecular weight lactic acid polymer as used, the weight-average molecular weight of the lactic acid polymer after hydrolysis and the weight-average molecular weight and the molecular weight fractions of the objective lactic acid polymer as obtained are shown in Table 1.

Examples 2 to 6

In the same manner as in Example 1, the lactic acid polymer of the invention was prepared. The weight-average molecular weight of the high molecular weight lactic acid polymer as used, the weight-average molecular weight of the lactic acid polymer after hydrolysis and the weight-average molecular weight and the molecular weight fractions of the objective lactic acid polymer as obtained are shown in Table 1.

TABLE 1

| | | Ex. 1 | Ex. 2 | Ex. 3 | Ex. 4 | Ex. 5 | Ex. 6 |
|---|---|---|---|---|---|---|---|
| Mw of high molecular weight lactic acid polymer used | | 40500 | 43600 | 40400 | 43300 | 38600 | 55000 |
| Mw of lactic acid polymer after hydrolysis | | 22200 | 22000 | 22700 | 22200 | 18600 | 27200 |
| Mw of lactic acid polymer obtained | | 22900 | 22000 | 21900 | 22300 | 19400 | 28200 |
| molecular weight fraction (%) | 1-1000 | 0.03 | 0.07 | 0.00 | 0.01 | 0.08 | 0.04 |
| | 1-3000 | 0.95 | 1.12 | 0.87 | 0.90 | 1.45 | 0.62 |
| | 1-5000 | 3.86 | 4.17 | 3.89 | 3.92 | 4.89 | 2.50 |

From Table 1, it is understood that the lactic acid polymers as obtained according to the process of the present invention comprise not more than about 5% by weight of the polymer having not more than 5,000 in weight-average molecular weight, not more than about 1.5% by weight of the polymer having not more than 3,000 in weight-average molecular weight and not more than about 0.1% by weight of the polymer having not more than 1,000 in weight-average molecular weight.

INDUSTRIAL UTILIZATION

The lactic acid polymer of this invention which comprises not more than about 5% by weight of the polymer having not more than 5,000 in weight-average molecular weight is useful as a matrix for mainly sustained-release drug preparations. The sustained-release microcapsule preparation encapsulating a physiologically active substance therein produced by the use of said lactic acid polymer can fully prevent the initial excessive release of the physiologically active substance from the microcapsules and keep effectively a stable release rate over a long period of time.

The invention claimed is:

1. A pharmaceutical composition, which comprises a lactic acid polymer precipitated out of a reaction solution with isopropyl ether, the lactic acid polymer being 20,000 to 25,000 in weight-average molecular weight and the content of lactic acid polymers having not more than about 5,000 in weight-average molecular weight in the lactic acid polymer being not more than about 5% by weight.

2. The pharmaceutical composition according to claim 1, wherein the content of lactic acid polymers having not more than about 3,000 in weight-average molecular weight in the lactic acid polymer being not more than about 1.5% by weight.

3. The pharmaceutical composition according to claim 2, wherein the content of lactic acid polymers having not more than about 1,000 in weight-average molecular weight in the lactic acid polymer being not more than about 0.1% by weight.

4. The pharmaceutical composition according to any one of claims 1 to 3, which is a sustained-release preparation.

5. The pharmaceutical composition according to any one of claims 1 to 3, which is a microcapsule.

6. The pharmaceutical composition according to claim 1, which comprises a physiologically active peptide or a salt thereof.

7. The pharmaceutical composition according to claim 6, wherein the physiologically active peptide or the salt thereof is a luteinizing hormone releasing hormone (LH-RH) derivative or a salt thereof.

8. The pharmaceutical composition according to claim 6, wherein the physiologically active peptide or the salt thereof is leuprorelin or a salt thereof.

9. The pharmaceutical composition according to claim 7 or 8, which is used for treatment or prevention of prostatic cancer, prostatic hyperplasia, endometriosis, fibroid, precocious puberty or breast cancer.

10. The pharmaceutical composition according to claim 7 or 8, which is a sustained-release preparation retaining a stable release rate of a physiologically active peptide or a salt thereof over six months or more.

11. The pharmaceutical composition according to claim 6, wherein initial excess release of the physiologically active peptide or salt is prevented.

12. The pharmaceutical composition according to claim 1, wherein the reaction solution comprises dichloromethane.

* * * * *